United States Patent
Maltby et al.

[11] Patent Number: 6,062,070
[45] Date of Patent: *May 16, 2000

[54] METHOD AND APPARATUS FOR THE SONIC MEASUREMENT OF SLUDGE AND CLARITY CONDITIONS DURING THE TREATMENT OF WASTE WATER

[75] Inventors: Frederick L. Maltby, Jenkintown; Yang Wang, Bensalem, both of Pa.; Norman Nardelli, Morristown, N.J.; L. Jonathan Kramer, Warminster, Pa.

[73] Assignee: Drexelbrook Controls, Inc., Horsham, Pa.

[ * ] Notice: This patent issued on a continued prosecution application filed under 37 CFR 1.53(d), and is subject to the twenty year patent term provisions of 35 U.S.C. 154(a)(2).

[21] Appl. No.: 08/741,408
[22] Filed: Oct. 29, 1996
[51] Int. Cl.[7] ............................. G01N 29/02; G01S 15/14
[52] U.S. Cl. ...................... 73/61.49; 73/61.75; 73/61.79; 73/64.55; 73/290 V; 367/99; 367/908
[58] Field of Search ................................ 73/61.41, 61.49, 73/61.75, 61.79, 64.55, 290 V; 367/99, 908

[56] References Cited

U.S. PATENT DOCUMENTS

| | | | |
|---|---|---|---|
| 3,128,786 | 4/1964 | Badgett | 137/467.5 |
| 4,000,650 | 1/1977 | Snyder | 73/290 V |
| 4,031,743 | 6/1977 | Kossoff et al. | 73/67.8 |
| 4,121,094 | 10/1978 | DiVito et al. | 235/92 FL |
| 4,700,569 | 10/1987 | Michalski et al. | 73/290 V |
| 4,868,797 | 9/1989 | Soltz | 367/98 |
| 4,931,175 | 6/1990 | Krofta | 210/86 |
| 4,940,902 | 7/1990 | Mechalas et al. | 250/573 |
| 5,131,271 | 7/1992 | Haynes et al. | 73/290 |
| 5,142,504 | 8/1992 | Köster et al. | 367/99 |
| 5,150,334 | 9/1992 | Crosby | 367/99 X |
| 5,157,639 | 10/1992 | Leszczynski | 367/99 |
| 5,182,951 | 2/1993 | Jorritsma | 73/861 |
| 5,392,257 | 2/1995 | Gilmour | 367/135 |
| 5,421,995 | 6/1995 | Norcross | 210/86 |
| 5,601,704 | 2/1997 | Salem et al. | 210/104 X |
| 5,760,309 | 6/1998 | Maltby et al. | 73/646 |

OTHER PUBLICATIONS

Wilkinson, H.J., "Clarifier and Thickener Interface Control", Royce Instrumentation Corporation, 50 pages.

*Primary Examiner*—Daniel S. Larkin
*Attorney, Agent, or Firm*—Woodcock Washburn Kurtz Mackiewicz & Norris LLP

[57] ABSTRACT

A sludge blanket level is determined in a waste water treatment clarifier using sonic pulse reflections. Additionally, using similar techniques, the clarity of the waste water is determined. A sonic pulse is directed into the waste water. Echos are generated as the pulse encounters the impedance mismatches indicative of changes in the density of the water. The echos are compensated for attenuation as a function of travel time through the water, energy lost due to prior peak reflections, and are processed to remove random signals using correlation techniques. A sludge blanket is selected from the compensated echo signal as a function of the size and location of echo peaks. Additionally, the clarity is determined as a flnction of the area under the echo signal between two points corresponding to predefined levels in the clarifier tank.

25 Claims, 10 Drawing Sheets

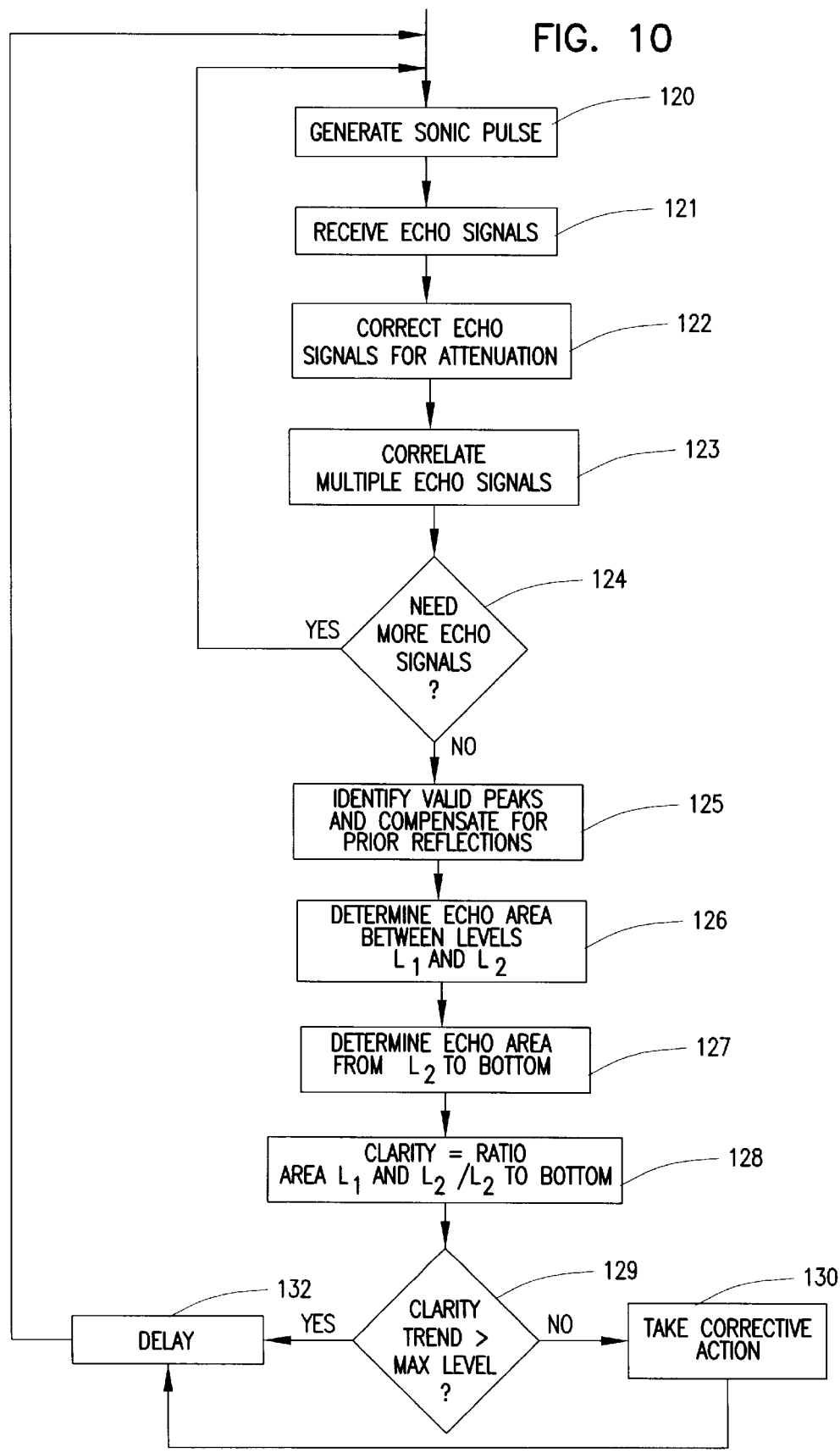

METHOD AND APPARATUS FOR THE SONIC MEASUREMENT OF SLUDGE AND CLARITY CONDITIONS DURING THE TREATMENT OF WASTE WATER

FIELD OF THE INVENTION

The invention relates to the detection of phase boundaries between layers of liquid using sonic energy. More particularly, the invention relates to a method and apparatus for detecting phase boundaries in a waste water clarifier for defining the level of a sludge blanket and the clarity of the clarifier.

BACKGROUND OF THE INVENTION

A process of removing semi-solid material from water, often referred to as waste water treatment, is used to treat waste water from manufacturing processes, sewage and the like. To that end, a variety of techniques have been developed and used in the treatment of waste water. One popular technique incorporates a settling tank (alternately referred to as a clarifier) that separates semi-solid material (popularly known as sludge) from the water via gravity. Using this technique, the waste water (influent) enters a clarifier, wherein the sludge is encouraged to settle to the bottom. As the sludge settles, density gradient layers form in the clarifier, with the densest layers disposed toward the bottom of the clarifier. Relatively clear water then exits from the top of the clarifier, while the sludge is removed from the bottom.

Controlling the level of sludge is a key aspect in the effective operation of the clarifier. On the one hand, if the sludge level is too high, contaminated water may exit from the top of the clarifier. On the other hand, if the sludge level is too low, the sludge removed from the bottom of the tank will contain too much water, increasing disposal costs.

Consistently determining the location of a "sludge blanket"—an industry term used to refer to a demarcation level in the clarifier—is the key aspect to controlling the sludge level within the clarifier. The material above the sludge blanket is, in theory, mostly liquid and is more clear; whereas, the material below the sludge blanket is, in theory, mostly solid and is relatively dense. Although the name implies that the sludge blanket location may be readily determined, in practice the determination is less than precise. The challenge in determining the sludge blanket location arises from the nature of the density gradients in the clarifier. That is, the material in the tank is thinnest near the top and densest near the bottom; however, there is no absolute demarcation point where the clear water ends and the sludge begins. Consequently, the techniques currently employed to measure the sludge blanket level provide inconsistent results. This inconsistency leads to inefficient treatment of waste water.

Although determining a sludge blanket level is a significant aspect of waste water treatment, where and how that level is maintained presents trade-offs for the waste water treatment plant operator. One of the most significant trade-offs concerns determining at what level to maintain the sludge blanket. On the one hand, maintaining a high sludge blanket level generally increases the density of the sludge in discarded waste water and results in reduced disposal costs. The disposal costs are reduced because the sludge within the sludge blanket is disposed of when it accumulates to a predetermined level in the bottom of the tank. The disposal cost of the sludge is directly influenced by the percentage of solid material in the discarded waste. The denser the sludge, the more economical the disposal and vice-versa. As a result, disposal costs are decreased because less excess water is transported and disposed with the sludge. As a rule of thumb, sludge blanket densities typically range from 1 to 5 percent solids. If the sludge blanket is too low or non-existent, the sludge removed from the tank will be about 99 percent water. If a high sludge blanket level is maintained in the clarifier the underlying sludge is generally denser. Thus, there is a strong economic incentive to maintain a high sludge blanket.

On the other hand, current systems that increase sludge density by maintaining a high sludge blanket level have the unfortunate side-effect of increasing the likelihood that contaminated water will exit the tank. That is, as the sludge level rises, the likelihood increases that the water exiting the clarifier will be less clear. So as a trade-off to maintaining a high sludge blanket, closer scrutiny of the clarifier is required because of the potential for short-circuiting the tank, wherein suspended solids do not settle but rather exit out of the top of the clarifier. Such short circuits generally result in downstream pollution and can be the basis for violations of governmental pollution regulations. Thus, there is a need for a system that allows the sludge level to be maintained at a high level, while having an accurate and economical monitoring system.

Several methods have been employed at waste water treatment plants to monitor the sludge blanket level. Among the most widely used—and the most primitive—is a "sludge judge." A sludge judge is a tube that takes a core sample of the clarifier. In operation, the sludge judge is slowly lowered into the water allowing a representative core sample of the water to enter the tube. When the sludge judge has reached the bottom of the tank, the tube is closed and removed from the tank. The translucent tube is then visually inspected and the operator makes a subjective determination of the location of the sludge blanket. The problems with such a technique for monitoring the sludge blanket are numerous and, perhaps, obvious. For example, errors are introduced if the tube is not lowered at the proper rate or angle. Additionally, different sludge blanket determinations will result from taking the core sample at different locations in the tank or from different operators making the determination, which leads to a variable and subjective sludge blanket determinations.

Other devices use portable sonic or optical sensors to determine the sludge blanket location. U.S. Pat. No. 4,940,902 issued to Mechalas et al. discloses such a device. The device consists of a transmitter and a receiver pair (either sound or light), which is lowered into the tank. As the density of the waste water increases, the operator monitors the lowering of the device and the corresponding density either audibly, via a meter or via some other indicator. Although, such devices overcome some of the problems encountered in the use of a sludge judge, additional problems arise. For example, the device must physically enter the sludge blanket. This could agitate the sludge sediment and lead to a false reading. Moreover, as with the sludge judge, different operators may obtain different readings through human error.

In U.S. Pat. No. 4,121,094 issued to DiVito et al., a technique is described for using ultrasonic energy to measure the sludge blanket level. According to the DiVito patent, a transducer is mounted near the top of the tank. The transducer is capable of both transmitting and receiving an ultrasonic signal which is projected toward the sludge blanket. The signal reflected from the sludge blanket is received by the transducer and converted to an electrical signal. However, the DiVito technique is not sufficiently accurate.

For example, the sludge blanket is detected by comparing the electrical signal received from the ultrasonic echo to a reference voltage. When the amplitude of the echo signal matches the reference voltage, the DiVito system interprets this as the sludge blanket having reached the maximum height. Pumps are then operated to lower the sludge blanket level. Such a technique may falsely detect transient conditions as a sludge blanket level. For example, sludge disturbed by the skimmer arm could cause the pump to falsely operate. Moreover, thin layers of sludge could bypass detection and exit the top of the clarifier.

All of the techniques described above suffer from the inability to accurately and consistently maintain sludge levels in a clarifier. Applicants have recognized that method and apparatus that could increase the density of disposal sludge while preventing sludge from short-circuiting the tank would greatly enhance the efficiency of waste water treatment plants. Thus, there is a long-felt need for method and apparatus that accurately and consistently maintain the sludge levels within a clarifier.

SUMMARY OF THE INVENTION

The present invention meets the needs above by providing a method and apparatus for use in connection with level measurement in a medium that has impedance mismatches, such as those found in a clarifier for waste water treatment. The invention operates on acoustic echoes that are generated when acoustic energy transmitted into the medium encounters the impedance mismatches caused by density changes of the medium.

The method of using sonic energy to measure the impedance mismatches comprises the steps of receiving the echoes and converting them into electrical representations that have magnitudes indicative of amplitudes of the echoes. The magnitudes of the electrical representations are then adjusted according to a first function that is inversely related to attenuation of acoustic energy occurring during travel of the acoustic energy through the medium. This first function could be accomplished via hardware or software. In a hardware implementation, an amplifier, employing the first function as a gain characteristic of the amplifier, could be used. In such a case, the gain characteristic is such that the gain of the amplifier increases in relation to times that echoes are received. After compensating the electrical representations according to the first function, selected ones of the adjusted magnitudes are further adjusted according to a second function that compensates the adjusted magnitudes under consideration for attenuation of acoustic energy caused by acoustic energy reflected in generating previous echoes. This second function could be accomplished by obtaining an indication of the acoustic energy reflected in generating the previous echoes and increasing the indication to the adjusted magnitudes under consideration.

The method above has many applications. For example, the adjusted electrical representations could be further processed to determine the approximate level of a selected portion of the medium, e.g., a sludge blanket in a waste water treatment clarifier. After determining the level, sludge blanket or otherwise, an alarm could be set indicating a level above a predefined value, e.g., a sludge blanket level that is too high.

The methods described above could be applied in a waste water treatment plant that uses a clarifier to filter waste water. As indicated above, such a method would be employed to substantially define the location of a sludge blanket in the clarifier. As such, a sonic pulse is transmitted toward the bottom of the clarifier in a path substantially normal to the surface of the waste water. The resulting echo signal is then received and processed to determine the sludge blanket level. According to aspects of the invention, the echo signal received is compensated for sonic pulse attenuation as a function of sonic pulse travel time through the waste water and pulse attenuation caused by cumulative reflections. The sludge blanket is then detected according to the size and location of the peaks.

According to a further aspect of this method, the peaks are compensated for cumulative reflections in several steps. First an amplitude, $A_{(i)}$ for each peak, i, in the echo signal is determined. Second, a distance, $L_{(i, i+1)}$, between each adjacent pair of peaks, i and i+1 is ascertained. Finally, a compensated amplitude, $A_{(i+1)}'$, is determined by compensating each amplitude $A_{(i+1)}$ for the energy absorbed by each prior peak i according to:

$$A_{(i+1)}'=A_{(i+1)}*\{1+K*L_{(i, i+)}*[A_{(i)}'/(A_{(i)}'+A_{(i+1)})]\},$$

where K is a constant.
Additionally, correlation is employed to filter random echo signals from the return signal.

As such, at least two echo signals are multiplied to create a single composite echos signal such that random changes in either echo signal are canceled.

According to another aspect of the invention, the techniques above are employed to determine the clarity of waste water within the clarifier. That is, a sound pulse is transmitted toward the bottom of the clarifier in a path substantially normal to the surface of the waste water. The echo signal is received and processed for waste water clarity. The processing comprises compensating the echo signal received for pulse attenuation as a flnction of sound pulse travel time through the waste water and amplifying the echo signal within a range corresponding to a first predefined level and a second predefined level. The clarity is then determined as an integral of the echo signal between the first predefined level and the second predefined level. The clarity could be employed, for example, to set an alarm condition when the integral is greater than a predefined value for a predefined period of time.

The apparatus for determining a sludge blanket level and clarity in a clarifier tank comprises a transmitter, a receiver, and various signal compensation means. The transmitter transmits a sonic pulse substantially normal to an expected level of the sludge blanket. The receiver then receives an echo signal of the sonic pulse, the echo signal being representative of changes in the concentration of contaminants within the water. The receiver also converts the echo signal into an electrical signal. Thereafter, first means in electrical communication with the receiver compensates the electrical signal for sonic pulse attenuation as a function of time (i.e., distance traveled through the water). Such compensation means can be accomplished via hardware or software. For example, an operation amplifier having a time varying gain could be employed. Second means are also provided to compensate the electrical signal for energy changes experienced by the sonic pulse as a function of cumulative previous echoes, which echoes are caused by changes in contaminant concentration. The electrical signal is then processed to determine the sludge blanket level as a function of the peaks within the electrical signal or clarity of the waste water. In one such function, the sludge blanket is selected as a weighted average of the magnitude of the peaks and their respective distances from the bottom of the clarifier.

In a preferred embodiment, the second means is accomplished via software. Accordingly, an analog-to-digital converter is employed to convert the electrical signal into a digital representation. A microprocessor, coupled to the analog-to-digital converter, executes a software program that detects peaks in the converted electrical signal and increases selected peaks by an amount related to the magnitude of prior peaks.

BRIEF DESCRIPTION OF THE DRAWINGS

The foregoing summary, as well as the following detailed description of the preferred embodiment, is better understood when read in conjunction with the appended drawings. For the purpose of illustrating the invention, there is shown in the drawings an embodiment that is presently preferred, it being understood, however, that the invention is not limited to the specific methods and instrumentalities disclosed.

In the drawings.

DETAILED DESCRIPTION OF A PREFERRED EMBODIMENT

According to a presently preferred embodiment a waste water treatment system that incorporates a control system based on sludge densities will now be described with reference to the FIGURES. It will be appreciated by those of ordinary skill in the art that the description given herein with respect to those FIGURES is for exemplary purposes only and is not intended in any way to limit the scope of the invention. For example, sample sonic pulse frequencies and durations are provided throughout the description. However, such examples are merely for the purpose of clearly describing the present invention and are not intended as limits.

I. SYSTEM OVERVIEW

Figure 1:
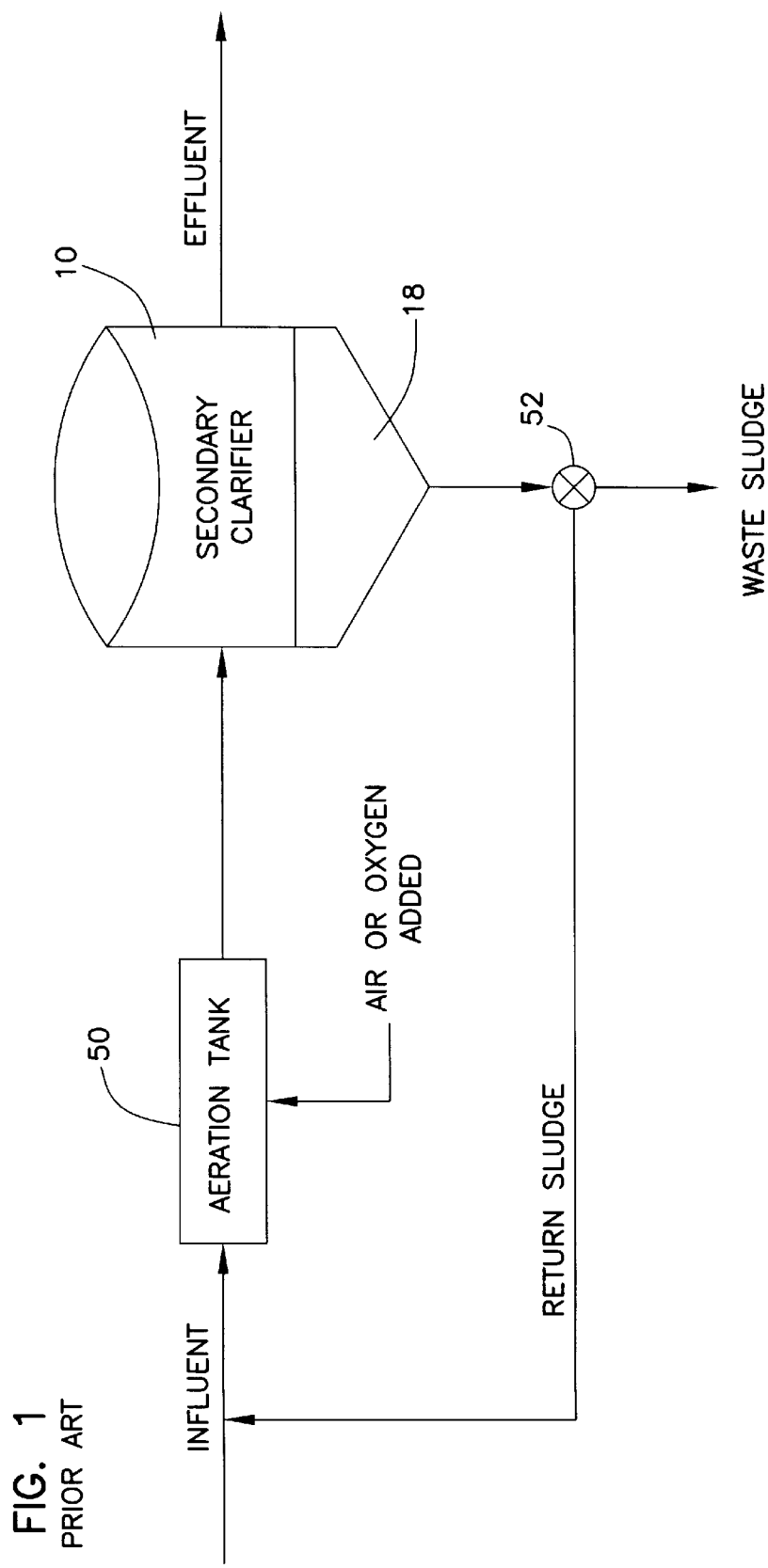
FIG. 1 is a block diagram of a portion of a waste water treatment plant wherein the present invention may be employed.

Referring now to the drawings wherein like numerals indicate like elements throughout, FIG. 1 depicts a portion of a prior art waste water treatment system. Typically, raw waste water first enters a primary clarifier (not shown) wherein floatable matter, solids and the like are removed. Thereafter, the output of the primary clarifier enters an aeration tank 50. In the aeration tank 50, the organic matter of the waste water is brought into contact with microorganisms. Oxygen is also added to the aeration tank 50. The organic matter and the oxygen become energy sources for the growth of the microorganisms. The resulting biological mass, commonly referred to as mixed liquor suspended solids (MLSS), then exits the aeration tank 50 and enters the secondary clarifier 10. Within the clarifier 10 the suspended solids settle to the bottom forming sludge layers 18. The water that exits the clarifier 10 in the effluent stream should be "clear" in the sense that it meets governmentally defined quantities of suspended solids in parts-per-million. In most previous waste water treatment systems, of which FIG. I is typical, the monitoring of the sludge layers is a manual task and the controlling of the system of FIG. I is performed manually by an operator, e.g. by turning on a pump (not shown) connected to valve 52 to remove sludge.

A sludge blanket 18 must be maintained at a predefined level to ensure proper operation of the clarifier 10. As such, the pump connected to valve 52 must be operated to raise or lower the sludge blanket 18 in accordance with the predefined level. By operation of the pump, a portion of the removed sludge is returned to the aeration tank 50 to maintain the biological microorganisms and, a portion of the sludge is removed from the system and discarded. As will be explained more fully below, the present invention provides for an efficient operation of the waste water treatment plant by automatically monitoring the sludge blanket 18 and maintaining a measure of the clarity of the clarifier 10. This monitoring information can then be used as part of a more automated waste water treatment plant.

Figure 2:
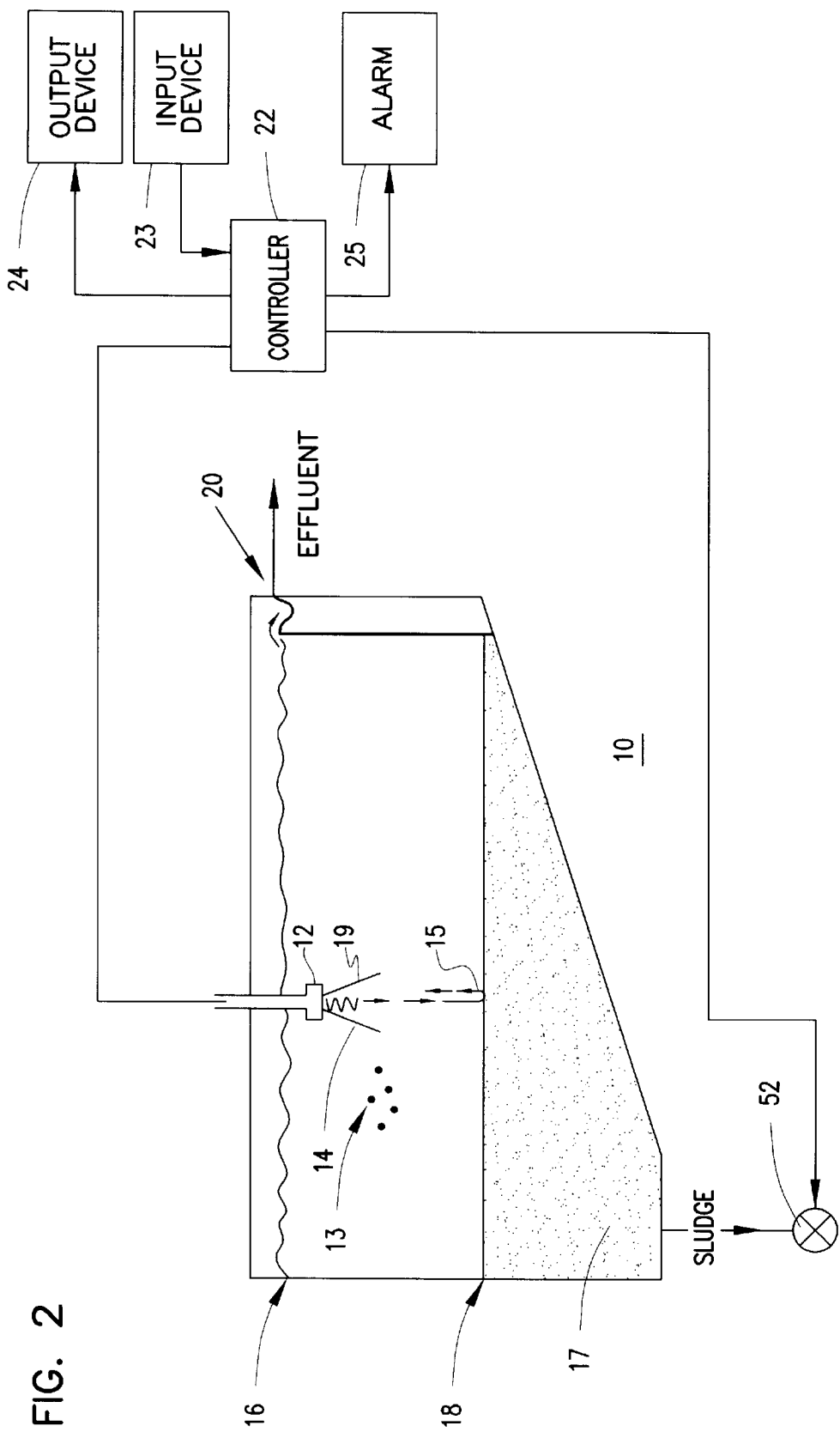
FIG. 2 is a pictorial representation of a clarifier tank employing aspects of the present invention.

Referring now to FIG. 2, the clarifier 10 and the system of monitoring the sludge blanket 18 in accordance with the present invention are depicted. As shown, the MLSS in the clarifier 10 separates into clear water, which exits the clarifier 10 in the effluent stream, and sludge 17 which exits the clarifier 10 under the control of valve 52. As noted above, if the sludge level rises too high within the clarifier 10, the effluent could become contaminated. Therefore, a sludge blanket 18 must be defined and maintained at a level that will keep the clarity of the effluent within governmental regulations. Also depicted in the clarifier 10 is a particular form of suspended solids 13, commonly referred to as fluff 13. Fluff 13 comprises particles relatively large in size but less dense than the sludge. As a result, the fluff 13 does not readily settle to the bottom of the clarifier 10.

Significantly, as the sludge blanket level rises, the fluff 13 also rises, increasing the potential that the fluff 13 will exit the clarifier 10 and contaminate the effluent.

As will be described more fully below, an operator (not shown) enters a desired sludge blanket set point into controller 22 via an input device 23, such as a keypad. The controller 22 then periodically monitors the sludge blanket level 18 via transducer 12 and displays the level 18 via an output device 24, such as an LCD display. Moreover, the controller 22 compares measured sludge blanket level 18 to the operator set point. If the measured sludge blanket level 18 is significantly higher than the set point, the controller 22 takes corrective action, such as operating the pump connected to valve 52, or sounding alarm 25 or both. Additionally, the controller 22 periodically monitors the water in the area above the sludge blanket 18 for suspended solids 13. If suspended solids 13 are detected at a predefined height in the clarifier 10, the controller 22 takes corrective action or sounds the alarm 25 or both.

II. MONITORING THE SLUDGE BLANKET

The clarifier 10 monitoring process begins when the controller 22 signals the transducer 12 to generate an sonic pulse 14 (hereinafter also referred to as a sonic pulse or sound pulse). That sonic pulse 14 then travels through the waste water contents of clarifier 10 in a direction substantially perpendicular to the water level 16. During its travel through the waste water, the sonic pulse 14 will encounter a variety of impedances, depending upon the varying sludge concentrations in the waste water. As the sonic pulse 14 experiences changes in the sludge concentration at various points, a corresponding change in impedance is experienced by the sonic pulse 14. Consequently, a portion of the sonic pulse 14 reflects back in the general direction of the transducer 12, and a portion of the sonic pulse 14 continues down into the clarifier 10. The reflected pulse results in echo 15, which is received by the transducer 12. The energy in the echo 15 excites the transducer 12, which in turn, converts the echo 15 into an electrical echo signal. The electrical echo signal is then provided to controller 22 for processing. After controller 22 collects a sufficient number of echo signals, the controller 22 employs further aspects of the present invention, which will be described in detail below, to determine the location of the sludge blanket 18 within the clarifier 10.

Figure 6:
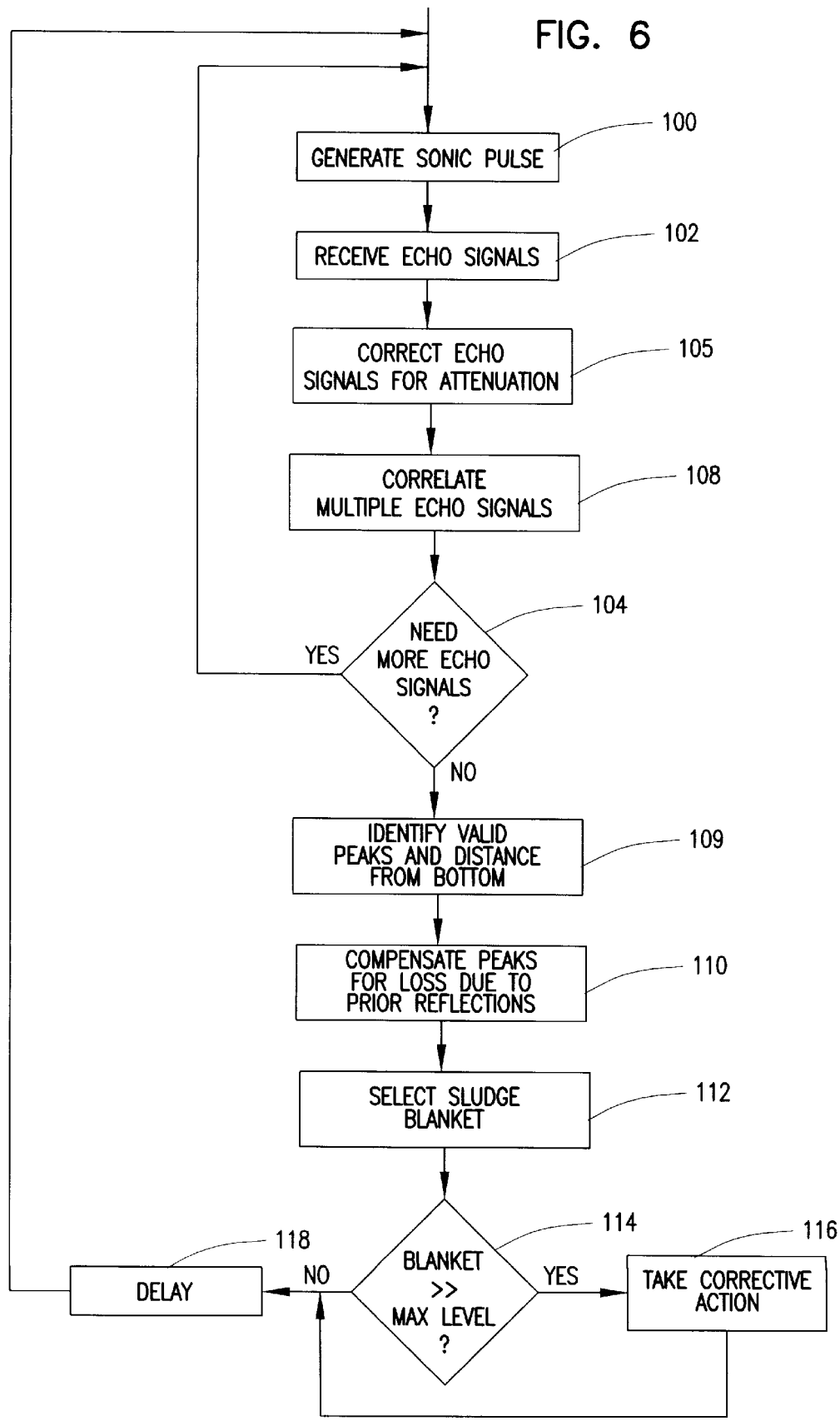
FIG. 6 is a flow chart of the process of determining the sludge blanket level in accordance with the present invention.

FIG. 6 presents a flow chart of the process employed by controller 22 for determining the sludge blanket 18 level. In the initial step 100, a sonic pulse 14 is generated, as described above, by exciting a transducer 12, such as a piezoelectric transducer, and directing it toward the expected location of the sludge blanket 18. In the presently preferred embodiment, a 200 kHz square wave is applied to the transducer for $100\mu$ seconds. As a result, 200 kHz sinusoidal waves issue from transducer 12 for about $100\mu$ seconds followed by a $500\mu$ second ring down.

Figure 8:
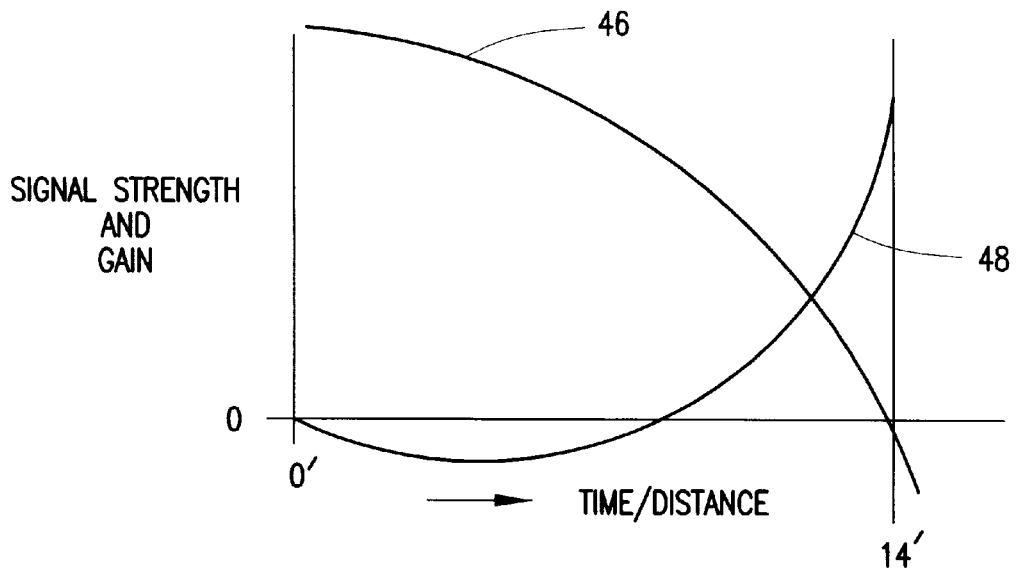
FIG. 8 graphically depicts the effects of pulse beam attenuation and the time varying gain that is applied to correct for the attenuation.

After the sonic pulse 14 is transmitted, the transducer 12 switches to a receive mode and begins listening for echoes 15 from the clarifier 10, as indicated at step 102. Three major procedures are performed during the reception of the echo 15 to ensure an accurate echo interpretation. The first procedure, as indicated by step 105, corrects the echo 15 for the effects of sonic energy attenuation due to distance traveled. That is, after the pulse exits the transducer, it is attenuated due to distance traveled and attenuated as a function of the square of the distance traveled from the transducer 12. As a result of distance traveled sonic pulse attenuation, each reflection that returns from deeper in the clarifier 10 is based on less available pulse 14 energy. Consequently, the intensity of early reflections is exaggerated relative to the intensity of later reflections. According to an aspect of the present invention, the echoes 15 received are normalized for the attenuation in the sonic pulse 14 due to distance traveled by amplifying the echo signal with a time varying gain factor (step 105). Referring also to FIG. 8, the strength of the sonic pulse 14 over time versus the time varying gain (TVG) factor that is applied to the echo signal is graphically illustrated. Time is plotted along the abscissa, while the pulse energy available, curve 46, and the gain applied, curve 48, are plotted along the ordinate. Notably, the TVG factor, represented by curve 48, is inversely related to the available energy of sonic pulse 14, represented by curve 46. By applying the TVG gain to the echo signal in this way, the echo signal is normalized for the clarifier depth. As will be described in further detail below, the TVG can be applied via an amplifier in series with the transducer 12 or, alternatively, the TVG can be applied via software.

In the second procedure, indicated by step 108 in FIG. 6, random signals are filtered from the echoes 15 received. Random conditions, such as noise or the movement of a skimmer arm within the clarifier 10, may create undesirable signals, which may inadvertently be perceived as sludge induced echoes. Therefore, according to an aspect of the present invention, the filtering is accomplished via a correlation technique wherein several echo signals are collected and compared by the controller 22 to remove the random signals. As a result of the correlation, a composite signal is generated that effectively cancels or minimizes the random signals. Effectively, sludge levels should appear static during the relatively short time period between successive pulses 14. Thus, an echo 15 from a change in sludge density should generally appear the same for two successive pulses 14. By contrast, random conditions will change between the two successive pulses 14 and, consequently, should not appear in successive echo signals. Thus, by multiplying the two echoes signals, those echoes appearing in both signals will remain, while the random conditions are diminished or canceled. As indicated by step 104, additional echo signals are gathered to correlate echoes.

Figure 3:
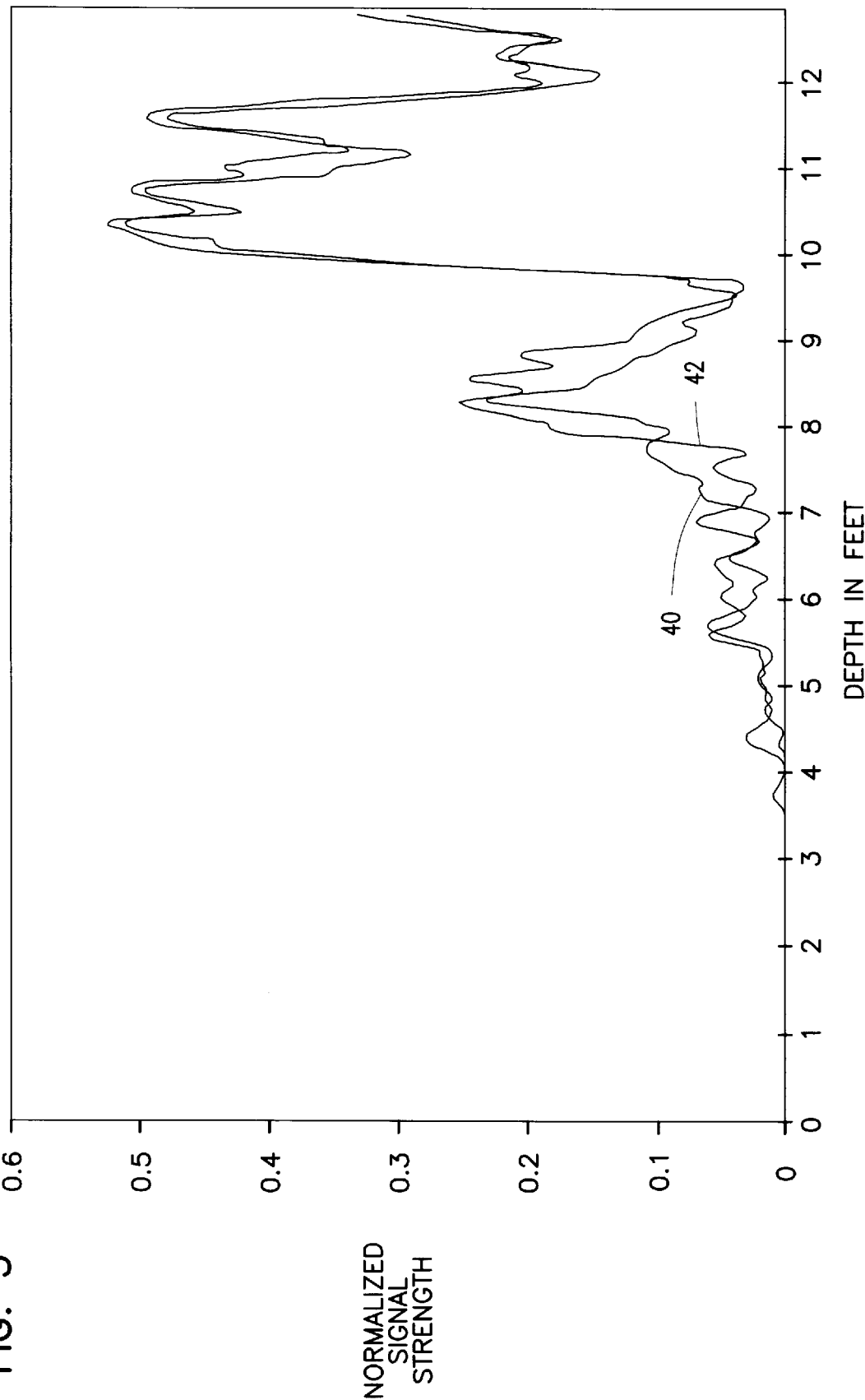
FIG. 3 is a graphical depiction of two exemplary normalized echo signals received in accordance with the present invention.
Figure 4:
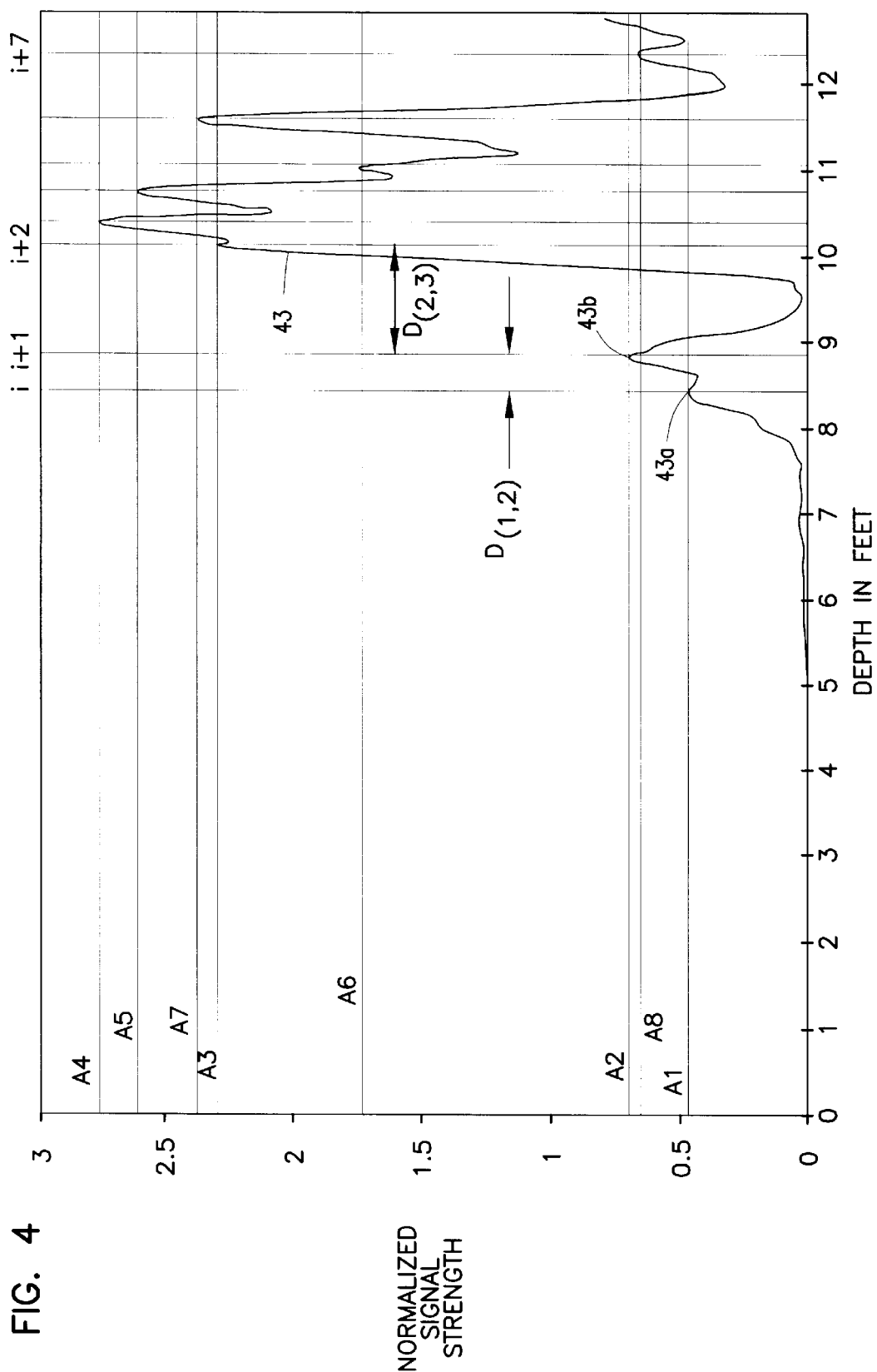
FIG. 4 is a graphical depiction of the correlation signal resulting from the combination of the exemplary echo signals depicted in FIG. 3.

FIGS. 3 and 4 graphically illustrates the process of using two echo signals to enhance the sludge blanket 18 determination. In the FIGURES, the depth of the clarifier 10 in feet is indicated along the abscissa, while normalized signal strength is indicated along the ordinate. FIG. 3 graphs two exemplary echo signals 40 and 42, which have been normalized for the effects of distance traveled. In FIG. 4, a composite echo signal 43 is graphed that was created by multiplying the two exemplary signals 40 and 42. By comparing the two FIGURES, it can be seen that those areas in which the two echo signals 40 and 42 agree are exaggerated, while the areas in which they disagree are minimized. As a result, the portions of the echo signal that are caused by sludge level induced impedance changes become more pronounced.

After all echo signals have been processed, valid peaks are detected in the compensated echo signal and the distance from the bottom of the clarifier is determined (step 109). The final procedure, compensates the echo signal for pulse 14 energy reflected by successive impedance changes, as indicated by step 110. That is, each time an impedance change is experienced by the sonic pulse 14, an echo 15 is generated. This echo 15 will appear as a local peak in the echo signal amplitude (see e.g., local peaks 43a and 43b of composite echo signal 43). Significantly, after each reflection, a portion of the energy from pulse 14 is directed back toward the transducer 12, while a portion of the energy from the pulse 14 continues down into the clarifier 10. The reflected energy is then unavailable to provide energy for later reflections. As a result, less energy will be reflected for subsequent impedance changes and the amplitude of the peak under consideration will not accurately reflect the magnitude of the impedance change experienced by the pulse 14. In other words, two identical impedance changes will generate different echo signals if generated by differing amounts of energy; the more available energy at the time of the reflection, the greater the echo strength. If left uncompensated, this phenomenon will skew the sludge blanket determination. Accordingly, before the sludge blanket can be accurately determined, the composite echo signal (e.g., signal 43) is compensated for this reflected energy loss.

In the presently preferred embodiment, the composite echo signal each peak, $A_{i+1}$, is compensated for reflected energy according to the following equation:

$$A'_{i+1} = A_{i+1}\left(1 + \left(KD_{(i,i+1)}\frac{A'_i}{A'_i + A_{i+1}}\right)\right) \quad (1)$$

Where:
  i is counter from 1 to the number of peaks detected in the composite echo signal;
  $A_i$ is the amplitude of ith peak in the composite echo signal;
  $A_i'$ is the compensated amplitude for the ith peak
  $D_{(i, i+1)}$ is the distance in feet between the peaks $A_i$ and $A_{i+1}$
  K is a constant as, explained below, that is based on the expected and measured sludge profile of the clarifier.

In essence, the equation compensates each peak under consideration for energy reflected in all preceding sludge density induced impedance changes, as represented by prior peaks. In addition to the peak compensation, the equation also factors in the thickness of each sludge layer, as indicated by the distance $D_{(i, i+1)}$ between the peaks.

The operation of the equation (1) can be better understood by reference to FIG. 4 wherein exemplary composite echo signal 43 is graphed. The first peak, $A_1$, remains uncompensated (i.e., the equation starts with i+1) because it is the first peak and as such the pulse 14 will not have experienced previous reflections. On the other hand, peak $A_2$, for example, should be compensated for the energy reflected by the previous sludge layer. Accordingly, energy reflected by peak $A_1$ will be added to peak $A_2$ as compensation. Moreover, the sludge density layer indicated by the peaks have a certain thickness (i.e. the distance from the start of one layer to the start of the next layer). This thickness is also accounted for by equation (1), as represented by $D_{(i, i+1)}$. Significantly, all subsequent peaks are compensated, according to the equation, for the energy reflected by all previous sludge layers. Thus, peak $A_3$ is compensated for energy reflected by peaks $A_2$ and $A_1$ and the distances $D_{(3,2)}$ and $D_{(2,1)}$; peak $A_4$ is compensated for energy reflected by peaks $A_3$, $A_2$ and $A_1$ and the distances $D_{(4,3)}$, $D_{(3,2)}$ and $D_{(2,1)}$; and so on until all peaks have been compensated.

The constant K is determined based on the clarifier profile. Essentially, there are three value ranges for K corresponding to three general clarifier profile classification: (1) the clarifier has a single dense sludge layer (K=0); (2) the clarifier has multiple sludge layers (K=1–8); and (3) the clarifier has a high number of thin sludge layers (K=9–10). The K value then is indicative of the level of material loss (the higher density and thickness of a layer the greater absorption takes place) encountered by the sludge blanket. The effect of a higher K value is to push the sludge blanket determination level further down into the tank.

Figure 5:
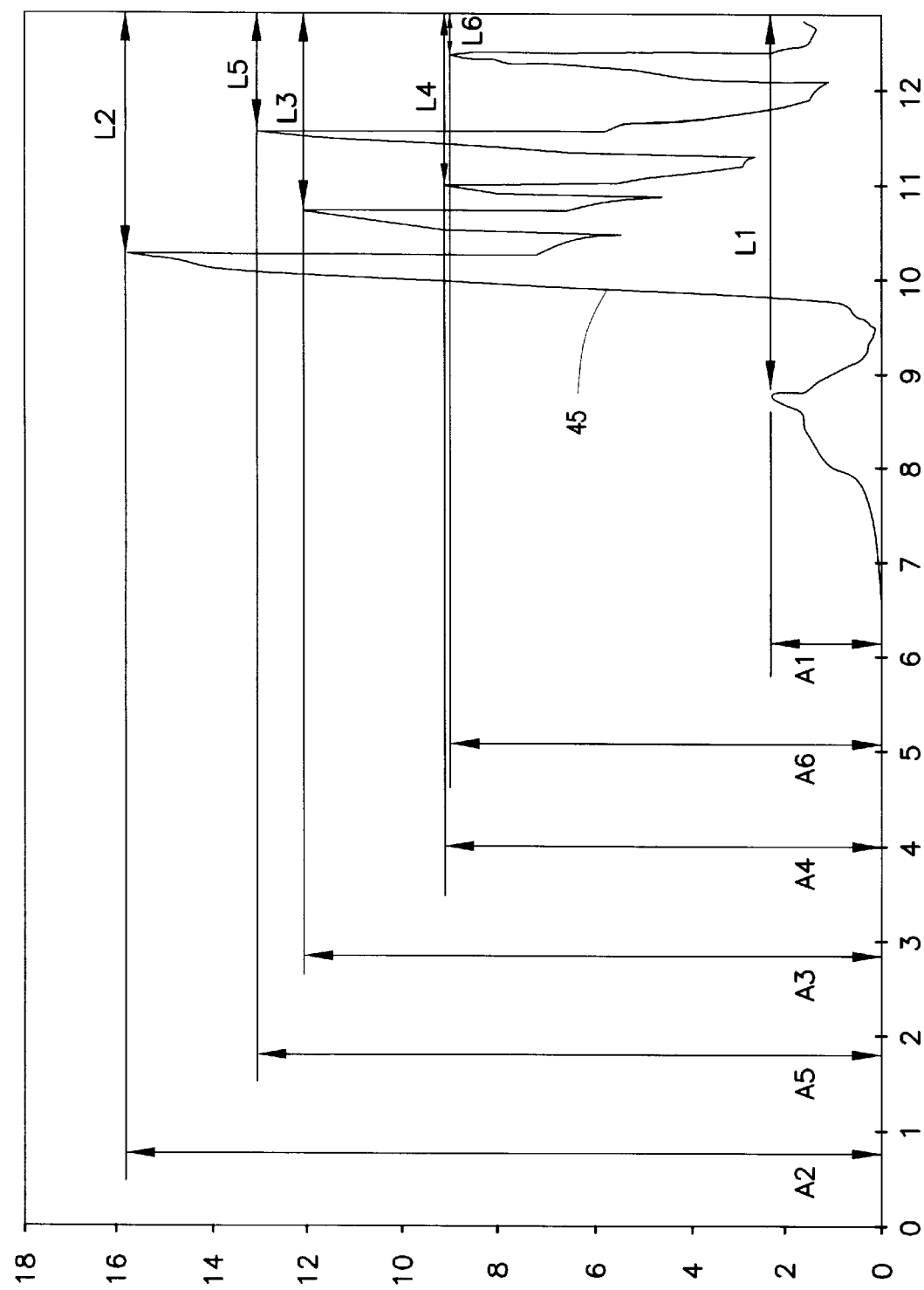
FIG. 5 is a graphical depiction of the correlation signals compensated for energy reduction due to prior echoes.

Referring also to FIG. 5, the compensated echo signal 45 is graphically illustrated, which signal resulted from applying equation (1) to the composite echo signal 43. The exemplary compensated signal 45 represents the culmination of compensations for sonic pulse distance traveled, random signals, and prior peak reflection as applied to the original echo signals 40 and 42 of FIG. 3.

As indicated at step 112 of FIG. 6, the sludge blanket 18 is then selected from this compensated echo signal, e.g., 45. Those skilled in the art will recognize that many variations are possible in selecting the sludge blanket 18 from the compensated echo signal, as exemplified by signal 45. For example, the peak with the greatest amplitude could be selected. However, in the presently preferred embodiment, the sludge blanket 18 is selected as the weighted average of the peaks of compensated echo signal (e.g., 45).

The determination of the sludge blanket level 18 is then determined according to the equation:

$$\frac{\sum_{i=1}^{n} (A'_i \times L_i)}{\sum_{i=1}^{n} A'_i} \quad (2)$$

Where:
  i is a number ranging from 1 to the number of peaks in the compensated echo signal;
  n is the number of peaks in the compensated echo signal;
  $A'_i$ is the amplitude of the ith peak; and $L_i$ is the level in feet from the bottom of the clarifier 10 for the ith peak.

As the equation implies, the selection of the sludge blanket 18 will depend on the density as well as the height in the clarifier of each sludge layer. Thus, the higher a sludge layer appears in the clarifier, the more weight it will be accorded. Significantly, even thin layers of sludge that rise up toward the top of the clarifier will cause the selection of a higher sludge blanket value 18. As a result, the likelihood is reduced that thin layers of sludge will rise up in the clarifier and contaminate the effluent.

After the sludge blanket level is determined, the value is compared to the sludge level input by the operator, step 114. If the blanket exceeds the input level for a significant time-period, which is determined by experimentation and input as a variable into the system, corrective action is taken, step 116. This corrective action may include sounding an alarm or operating a pump to lower the sludge blanket level. Otherwise, if the blanket level is acceptable, after a delay period, the process begins anew, step 118.

III. MONITORING CLARIFIER CLARITY

In addition to monitoring the sludge blanket level, the clarity of the clarifier must also be closely monitored to ensure the effluent remains within regulation. The clarity of the clarifier is a measure of the increases in suspended solids. As the suspended solids rise higher in the clarifier, the likelihood increases that some of the suspended solids will exit the clarifier and pollute the effluent. Such an event could lead to fines for violation of governmental regulations. The present invention, monitors the trend of suspended solids in the clarifier. As the trend increases above a predefined level, corrective action is warranted, e.g., an alarm is set or a pump is activated, diverting the effluent.

Figure 9:
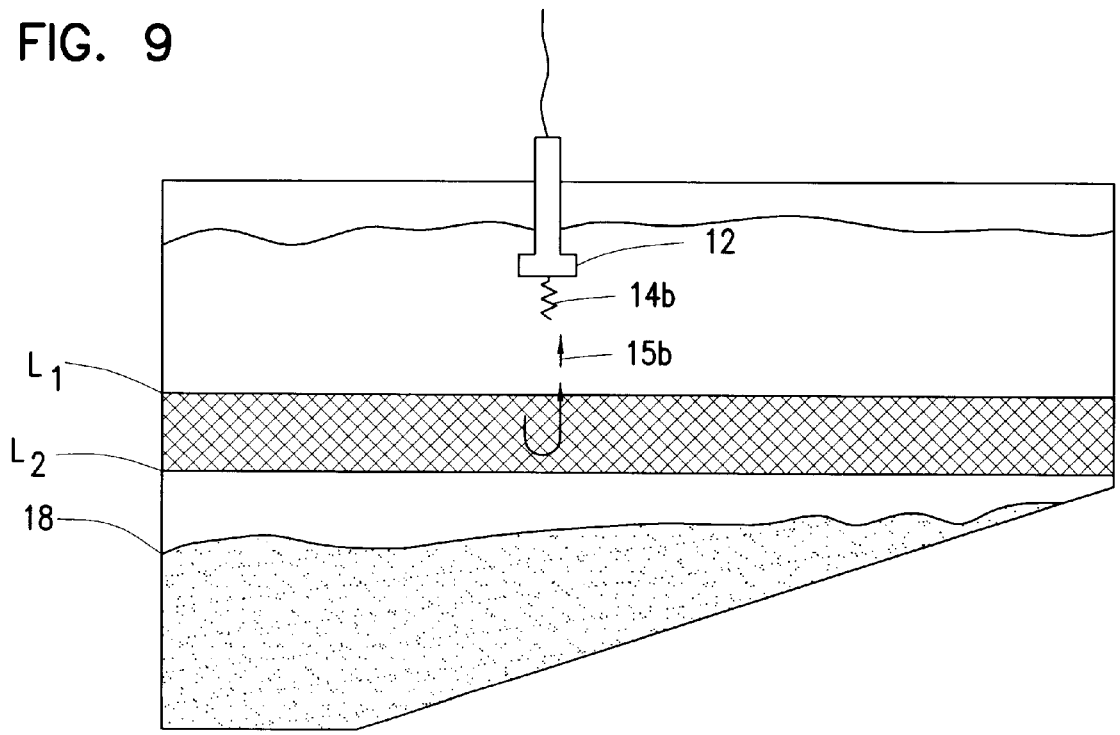
FIG. 9 illustrates the function of measuring the clarity of the clarifier in accordance with the present invention; and, FIG. 10 is a flow chart of the process for determining the clarity in accordance with the present invention.

Referring to FIG. 9, a clarifier 10 similar to the clarifier 10 illustrated in FIG. 2 is presented with the emphasis on illustrating the clarity monitoring function of the present invention. As shown, the area of the clarifier 10 between level L1 and L2 is monitored as a proxy for a clarity value of the tank. The levels L1 and L2 are operator selectable via input device 23. In general, a sonic pulse 14b, having the same characteristics as the pulse 14 used for monitoring the sludge blanket 18, is transmitted from transducer 12. The echo 15b that returns from the clarifier 10 is converted into an echo signal via transducer 12. As will be described more fully below, the echo signal is then processed for a clarity value, which is maintained by the controller 22 and monitored for the trend characteristics. If the trend line exceeds the operator selected threshold, corrective action is taken.

The processing of the echo signal for clarity shares many details with the sludge blanket 18 determination described in detail above. Essentially, the clarity determination shares all of the steps 100 through 110 of FIG. 6 that are employed in connection with the sludge blanket determination. For example, a sonic pulse is output. A TVG gain is applied. A correlation is employed to filter random signals. And, peaks are detected and compensated for losses due to prior reflections. After the echo signal has been processed, the clarity value is determined as an integral of the correlated echo signal between the L1 and L2. Therefore, a gain value is applied that exaggerates the echo signal between L1 and L2 so that a more accurate measurement can be obtained.

The process for controlling the clarifier clarity is best understood with reference to the flow chart of FIG. 10. Initially, a sonic pulse is transmitted and the echo signal is received, as described above in connection with the sludge blanket monitoring (repeated in this FIGURE as step 120–125). After the echo signal has been corrected, the clarity of the waste water in the clarifier is determined. The object of the clarity determination is to compare the value of the integral of the echo signal corresponding to the clarifier levels between L1 and L2 (step 126) to the value of the integral of the echo signal corresponding to the clarifier levels from L2 to the bottom of the clarifier (step 127). In the preset embodiment, in order to speed the calculation process, only the peak values are used. The equation is as follows:

$$\frac{\sum_{i=1}^{n} A_i}{\sum_{k=m+1}^{n} A_k} \quad (3)$$

Where:
A is the amplitude of a peaks in the echo signal;
1 is the number of the first peak in the echo signal corresponding to the region of the tank between L1 and L2;
m is the number of the last peak in the echo signal corresponding to the region of the tank between L1 and L2; and,
n is the last peak in the echo signal.

Accordingly, the equation generates a clarity value as the sum of the amplitudes of the peaks in the clarity region over the sum of the peaks in the region below the clarity region to the bottom of the clarifier (step 128). By generating the clarity value in this way, it is normalized for changes in the system dynamics, e.g., transducer power changes and the like. If the result of the equation indicates that the clarity trend value is too high (i.e., greater than a predefined limit), corrective action is taken (steps 129-130). Otherwise after a delay (on the order of 15 minutes to 1 hour) indicated at step 132, the process begins again.

After the sludge blanket level 18 and the clarifier clarity values are determined they are displayed on output device 24. If corrective action is required, a pump could be automatically operated until the clarity or sludge values return to a more acceptable level or an alarm could be set, indicating to an operator that corrective action is necessary. Obviously, the clarity and the sludge blanket determination share aspects in common. As such, the processes could be combined into a single clarifier tank monitoring system. For example, the same set of echo signals could be used in common and two sets of calculations then applied; however, they have been presented herein as separate processes for brevity and simplicity.

IV. CONTROLLER

Figure 7:
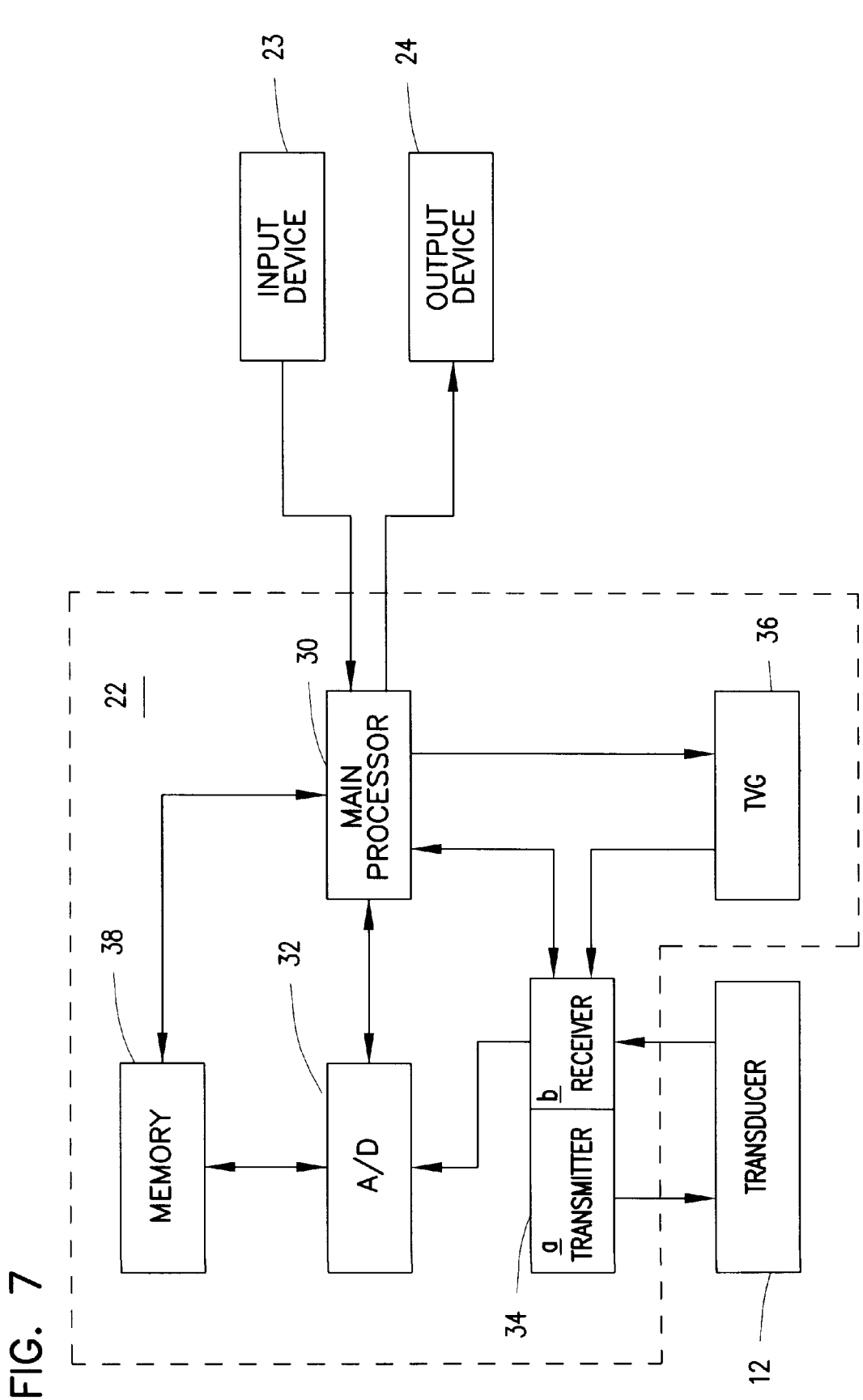
FIG. 7 is a block diagram of a system for generating the acoustic energy pulse and processing the echo signal.

The system for practicing the sludge monitoring processes is illustrated in FIG. 7. The system comprises an input device 23 whereby an operator (not shown) inputs variables, such as a sludge blanket set point, and a clarity set point and the like for use and storage by the controller 22. Input device 23 can be any conventional input device such as a keyboard, a mouse, or the like. Results and operator queries are presented on output device 24, which may be any conventional output device such as a monitor, an LCD display, or the like.

The controller 22 is comprised of a processor 30, memory 38, an A/D converter 32, a transceiver 34, and an amplifier 36. The main processor 30 provides the computing power needed by the controller 22 and can be any sufficiently powered CPU. In the presently preferred embodiment, the processor 30 is an 80C451 manufactured by Philips. The memory 38 provides for the storage of programs, user input variables, data gathered from the transducer and similar information. The memory 38 may be comprised of RAM, ROM, EEPROM, magnetic storage and the like. The A/D converter 32 is preferably an 8 bit A/D converter with an approximately 1.4$\mu$ second conversion time, such as a AD7820 manufactured by Analog Devices.

The processor 30 in conjunction with memory 38 executes the clarity and blanket measurements processes described above as a software program. For each clarifier echo signal, the processor 30 sends a start command to the transmitter portion of transceiver 34. The transmitter 34a comprises a square wave oscillator that oscillates at 200 kHz for 100$\mu$ seconds. The square wave is applied to the transducer 12 to generate a pulse 14. After about 600$\mu$ seconds, the transceiver 34 switches to a receive mode, wherein the transducer is coupled to an amplifier in the receiver 34b to begin converting echoes 15 into electrical signals. The output from the amplifier is connected to the A/D converter 32, which converts the echo signal into a digital form for processing by processor 30.

A TVG must be applied to the echo signal received in order to compensate the signal for pulse 14 attenuation due to distance traveled. Those skilled in the art will appreciate that the gain factor can be applied via software, i.e., after the echo signal has been digitized by the A/D converter 32, or via hardware. As is described more fully below, In a hardware embodiment, a synchronized square law waveform is generated which is used to set the gain of the amplifier of the receiver 34b. FIG. 8 presents the voltage waveform that is applied as the gain to the amplifier in the receiver 34b.

Figure 7A:
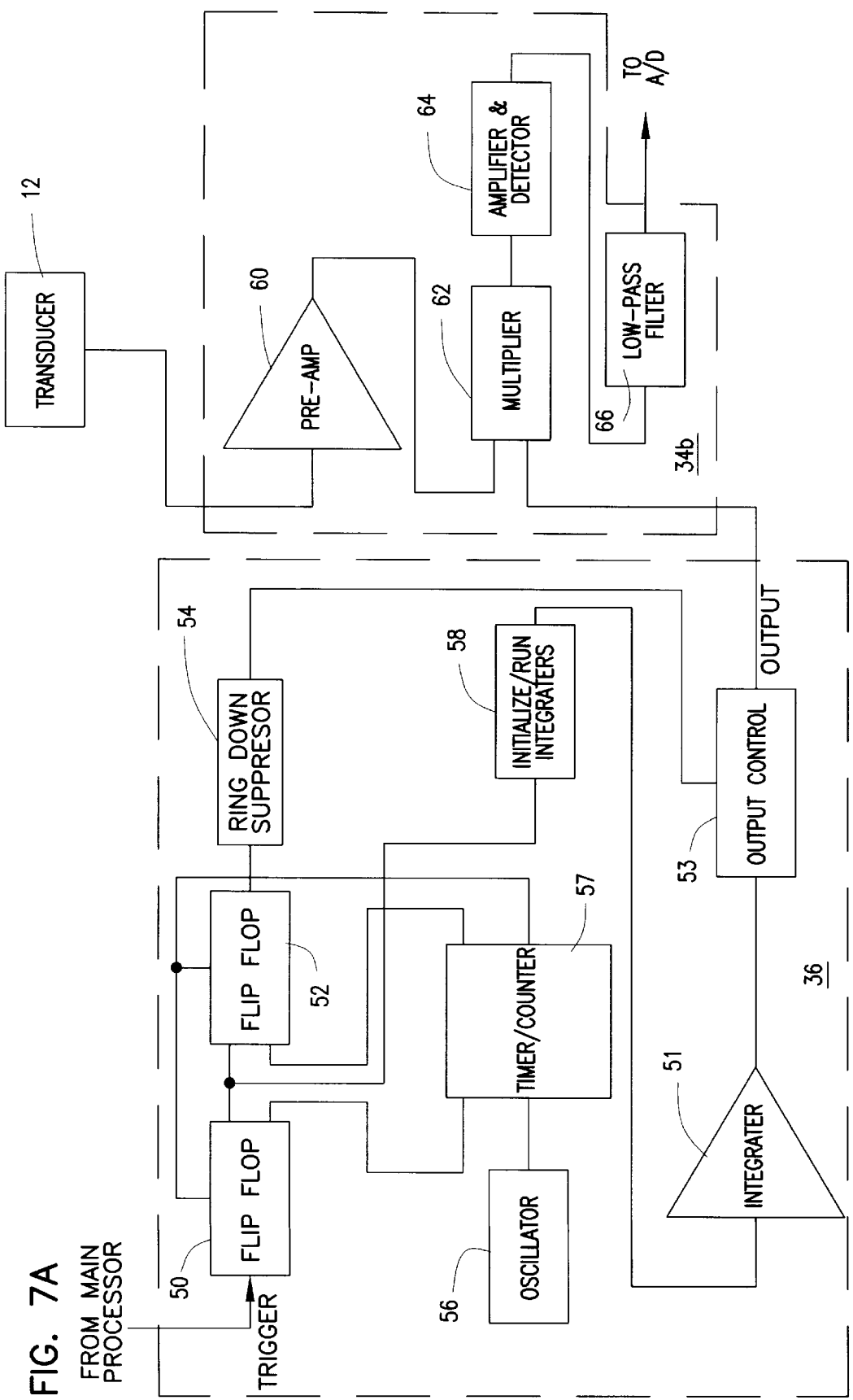
FIG. 7A is a block diagram of the function of the TVG mechanism and the receiver.

FIG. 7A is a block diagram of the TVG hardware connected to the receiver. Initially, the main processor 30 sends a trigger to the TVG to start the process. Thereafter, Flip-Flop 50 changes states, resetting the timer/counter 57 and sending a signal to Flip-Flop 52. The timer/counter 57 then begins providing a clock signal to Flip-Flop 52. Oscillator 56 provides a 50 kHz time base to timer/counter 57. At the end of a predefined period the timer counter sends a reset signal to the Flip-Flops 50, 52 so that they are ready for the next trigger signal. The output of Flip-Flop 52 provides the signal to output control 53 via ring-down suppressor 54. Output control 53 gates the TVG signal to the receiver 34b. However, ring-down suppressor 54, connected between Flip-Flop 52 and output control 53, ensures that no TVG signal is output until the transducer 12 has switched to receive mode. Simultaneously, Flip-Flop 50 provides a control signal to the initialization and integration control circuitry 58. This circuitry 58 provides a signal to integrator 51 to generate the TVG signal (as shown in FIG. 8) that is provided to receiver 34b.

FIG. 7A also shows further details of receiver 34b. The output from transducer 12 enters receiver 34b via a connection to pre-amp 60. Pre-amp 60 is tuned to the sonic pulse frequency (e.g., 200 kHz) and additionally provides a first stage of amplification. This ensures that only echo signals returning from the generated sonic pulse are received and amplified. The outputs from pre-amp 60 and TVG circuit 36 both feed multiplier 62 wherein both signals are multiplied together. As a result of the multiplication, the output from multiplier 62 is corrected for sonic pulse signal attenuation as a function of distance traveled. The multiplier output signal is then provided to amplifier and detector circuitry 64. Circuitry 64 detects the peaks of the echo signal by clamping or rectification of the echo signal. Additionally, circuitry 64 removes the carrier frequency of the sonic pulse (e.g., 200 kHz). Finally, the echo signal is low pass filtered (by filler 66) to further improve the signal to noise performance of the circuit. The final output signal is shown, for example, as curve 40 or 42 of FIG. 3.

The transducer 12, best shown in FIGS. 7 and 7A, comprises a commercially available device, such as a piezo-electric transducer. The operation of which is well-known to those skilled in the art. As such, the operational characteristics are left out of the present description for clarity and brevity. However, the placement of the transducer 12 is 1 to 2 inches below the water line 16 (see FIG. 2 for approximate location of the transducer with respect to the water line), ensuring that the operation of the present system is not affected by the air/water interface, and in a location no less than ⅓ or more than ½ the radius of the circular clarifier, ensuring more consistent measurements.

The system as described above has been installed and tested in the field at various waste water and water treatment facilities. The results achieved have met the performance characteristics as described herein. However, the present invention may be embodied in other specific forms without departing from the spirit or essential attributes thereof. For example, those skilled in the art will appreciate that the measurement techniques described herein could be used to measure sludge in the treatment of potable water. Accordingly, reference should be made to the appended claims, rather than to the foregoing specification, as indicating the scope of the invention.

What we claim is:

1. A compensation method for use in connection with level measurement in a medium, wherein acoustic echoes are generated when acoustic energy transmitted into the medium encounters impedance mismatches caused by density changes of the medium, the method comprising the steps of:

a) receiving the echoes and converting the same to electrical representations having magnitudes indicative of amplitudes of the echoes;
   b) adjusting the magnitudes of the electrical representations according to a first function that is inversely related to attenuation of acoustic energy occurring during travel of the acoustic energy through the medium; and,
   c) further adjusting at least selected ones of the adjusted magnitudes obtained in step (b) according to a second function that compensates one of the adjusted magnitudes under consideration for attenuation of acoustic energy caused by acoustic energy reflected in generating previous echoes.

2. Method according to claim 1 wherein step (b) comprises amplifying the representation via an amplifier, and the first function is a gain characteristic of the amplifier, the gain characteristic being such that the gain of the amplifier increases in relation to times that echoes are received.

3. Method according to claim 1 wherein step (c) comprises obtaining an indication of the acoustic energy reflected in generating the previous echoes and increasing the indication to the adjusted magnitudes under consideration.

4. Method according to claim 1 further comprising the step of determining the approximate level of a selected portion of the medium.

5. In a medium having a gradient density change, a method of defining a substantially planar level within said medium, comprising the steps of:

a) transmitting a sonic pulse substantially normal to an expected location of said planar interface;
   b) receiving an echo signal as a reflection of said sonic pulse comprising a plurality of peaks having magnitudes and locations indicative of density changes in the medium;
   c) normalizing said echo signal for sonic pulse attenuation as a fiction of travel time through said medium;
   d) multiplying each echo peak by the integral of each previously received echo peak to compensate each peak for the sonic pulse energy attenuation caused by previous reflections; and,
   e) selecting the planar level as a function of the magnitudes and locations of the peaks in the echo signals.

6. Method according to claim 5 wherein step (c) comprises amplifying the echo signal via an amplifier having a gain characteristic such that the gain of the amplifier increases in relation to time from the transmission of the sound pulse.

7. In a waste water treatment plant using a clarifier to filter waste water, a method of substantially defining the location of a sludge blanket in the clarifier, comprising the steps of:

a) transmitting a sonic pulse toward the bottom of the clarifier in a path substantially normal to the surface of the waste water;
   b) receiving an echo signal of said sonic pulse, wherein peaks of said echo signal define density changes in the waste water;
   c) compensating the echo signal received for sonic pulse attenuation as a function of sonic pulse travel time through the waste water;
   d) compensating the echo signal received for sonic pulse attenuation caused by cumulative reflections; and, e) selecting the sludge blanket from the compensated echo signal peaks according to the size and location of the peaks.

8. Method according to claim 7 wherein step (c) comprises amplifying the echo signal via an amplifier having a gain such that the gain of the amplifier increases in relation to time elapsed from transmission of the sonic pulse.

9. Method according to claim 7 wherein step (d) comprises obtaining an indication of the attenuation experienced by the sonic pulse as a result of reflection in generating the previous echo signals and increasing the echo signal relative to said indication.

10. Method according to claim 9, comprising the steps of:
i) finding an amplitude, $A_{(i)}$, for each peak, i, in the echo signal;
ii) finding a distance, $L_{(i, i+1)}$ between each adjacent pair of peaks, i and i+1;
iii) deriving an compensated amplitude, $A_{(i+1)}'$, by compensating each amplitude $A_{(i+1)}$ for the energy absorbed by each prior peak i according to:

$$A_{(i+1)}'=A_{(i+1)}*\{1+K*L_{(i, i+1)}*[A_{(i)}'/(A_{(i)}'+A_{(i+1)})]\},$$

where K is a constant.

11. In a clarifier tank containing water having a varying concentration of contaminants, a method of determining a point representing a sludge blanket level in the clarifier, comprising the steps of:
a) transmitting a sound pulse in a path substantially normal to the planar surface of the water in the clarifier tank, said sonic pulse projecting toward the surface of the sludge blanket;
b) receiving an echo signal of said sound pulse comprising a plurality of peaks;
c) compensating the echo signal received for attenuation of the sonic pulse as a function of distance traveled in the water;
d) finding an amplitude, $A_{(i)}$, for each peak, i, in the echo signal;
e) finding a distance, $L_{(i, i+1)}$, between each adjacent pair of peaks, i and i+1;
f) deriving a compensated amplitude, $A_{(i+1)}'$, by compensating each amplitude $A_{(i+1)}$ for the energy absorbed by each prior peak i according to:

$$A_{(i+1)}'=A_{(i+1)}*\{1+K*L_{(i, i+1)}*[A_{(i)}'/(A_{(i)}'+A_{(i+1)})]\},$$

where K is a constant; and,
g) selecting the sludge blanket level as a function of a weighted average of compensated amplitude and distance from a bottom of the tank.

12. Method according to claim 11, comprising the further steps of:
i) repeating steps (a–c) to obtain at least two echo signals
ii) correlating said at least two echo signals to create a single composite echo signal such that random changes in said at least two echo signals are canceled;
iii) repeating steps (d–f) for the composite echo signal.

13. An apparatus for determining the location of density gradients in a medium having a plurality of density gradients, comprising:
a transmitter for outputting a sonic pulse having a frequency, f;
a receiver tuned to the frequency f of said energy pulse for inputting an echo of said energy pulse, said echo representing changes in the density of the medium, wherein said receiver outputs an electrical signal as a function of said echo of said sonic pulse;
an amplifier coupled to said receiver for amplifying said electrical signal to compensate for energy pulse attenuation as a function of travel time through said medium; and,
means coupled to the amplified electrical signal for compensating the electrical signal for cumulative sonic energy attenuation caused by reflection in all previous density changes in the media.

14. Apparatus according to claim 13 wherein said means for compensating the electrical signal, comprises:
an analog-to-digital converter for converting said electrical signal to a digital representation; and,
a microprocessor coupled to said analog-to-digital converter, said microprocessor operating a software program that detects peaks in the converted electrical signal and increases selected peaks by an amount related to the magnitude of prior peaks.

15. Apparatus according to claim 13 wherein the amplifier comprises an operation amplifier having a time varying gain.

16. Apparatus according to claim 13 wherein the amplifier comprises:
an analog-to-digital converter for converting said electrical signal to a digital representation; and,
a microprocessor coupled to said analog-to-digital converter, said microprocessor operating a software program that increases said digital representation by a time varying gain.

17. An apparatus for use in measuring suspended solids in a waste water treatment plant, comprising:
a transmitter for transmitting a sonic pulse substantially normal to an expected level of the sludge blanket;
a receiver for receiving an echo signal of said sonic pulse, said echo signal representing a change in a concentration of contaminants within the water, and converting said echo signal into an electrical signal;
means for compensating said electrical signal for sonic pulse attenuation as a function of distance traveled;
means for compensating said electrical signal for energy changes experienced by the sonic pulse as a function of cumulative previous echos caused by changes in contaminant concentration; and,
means for determining the sludge blanket level as function of the magnitude and location of peaks within said electrical signal.

18. An echo compensation method for use in connection with level measurement in a container containing a medium, wherein echoes are generated when a burst of acoustic energy transmitted into the container encounters impedance mismatches in the medium caused by density changes of the medium, the method comprising the steps of:
a) receiving the echoes from said burst of acoustic energy and converting the same to electrical representations; and
b) adjusting at least selected ones of the electrical representatives of said echoes obtained in step (a) for acoustic energy reflected in previous echoes.

19. The method as recited in claim 18 further comprising the step of adjusting the electrical representations for travel of the acoustic energy through the medium.

20. The method as recited in claim 19 wherein step of adjusting for travel of the acoustic energy through the medium comprises amplifying the representation via an amplifier.

21. The method as recited in claim 20 wherein the adjustment is related to a gain characteristic of the amplifier, the gain characteristic being such that the gain of the amplifier increases in relation to times that echoes are received.

22. The method as recited in claim 18 wherein the step (b) comprises the steps of:
   (i) determining from a corresponding electrical representation a peak for substantially each echo received, wherein the peaks comprise a substantially maximum energy level for each echo; and
   (ii) compensating the selected ones of the electrical representations for energy reflected in previous echoes as a function of echo peaks as determined in step (i).

23. The method as recited in claim 22 further comprising the step of selecting a level in said medium from one of the selected ones of the compensated electrical representations according to the size and location of its peak.

24. The method as recited in claim 18 wherein the medium comprises water.

25. The method as recited in claim 18 wherein the container comprises a waste water treatment tank and the medium comprises water.

* * * * *